US012364839B2

(12) United States Patent
Azmat (10) Patent No.: US 12,364,839 B2
(45) Date of Patent: Jul. 22, 2025

(54) ALL-IN-ONE DELIVERY SHEATH/CATHETER—NOORCATH

(71) Applicant: Najam Azmat, Dacula, GA (US)

(72) Inventor: Najam Azmat, Dacula, GA (US)

( * ) Notice: Subject to any disclaimer, the term of this patent is extended or adjusted under 35 U.S.C. 154(b) by 0 days.

(21) Appl. No.: 18/981,958

(22) Filed: Dec. 16, 2024

(65) Prior Publication Data
US 2025/0195830 A1   Jun. 19, 2025

Related U.S. Application Data

(60) Provisional application No. 63/611,499, filed on Dec. 18, 2023.

(51) Int. Cl.
*A61M 25/01* (2006.01)
*A61M 25/00* (2006.01)

(52) U.S. Cl.
CPC ...... *A61M 25/003* (2013.01); *A61M 25/0029* (2013.01); *A61M 25/0136* (2013.01); *A61M 25/0147* (2013.01); *A61M 2025/0031* (2013.01); *A61M 2025/0039* (2013.01); *A61M 2202/0007* (2013.01); *A61M 2202/0468* (2013.01)

(58) Field of Classification Search
CPC ............ A61M 25/007; A61M 25/0133; A61M 25/0147; A61M 25/0136; A61M 2025/0004; A61M 2025/0039
See application file for complete search history.

(56) References Cited

U.S. PATENT DOCUMENTS

| | | | |
|---|---|---|---|
| 6,592,544 B1 * | 7/2003 | Mooney | A61M 39/24 604/35 |
| 8,808,345 B2 * | 8/2014 | Clark | A61B 34/74 607/113 |
| 9,901,710 B2 * | 2/2018 | Kassab | A61M 25/0084 |
| 11,364,365 B2 * | 6/2022 | Regnier | A61B 5/6861 |
| 2023/0082336 A1 * | 3/2023 | Sakakibara | A61F 7/12 607/105 |

* cited by examiner

*Primary Examiner* — Laura A Bouchelle
(74) *Attorney, Agent, or Firm* — BEKIARES ELIEZER LLP (57) ABSTRACT

A catheter system may include a dual lumen catheter. The dual lumen catheter may comprise an inner lumen configured to accommodate interventional devices and an outer lumen surrounding the inner lumen. The outer lumen may comprise a plurality of contrast injection ports and a shape-changing mechanism. Additionally, a rotation mechanism may be coupled to a proximal end of the dual lumen catheter and configured to rotate the dual lumen catheter. A locking mechanism may also be included, configured to maintain a shape of the dual lumen catheter. This system allows for enhanced control and functionality during medical procedures, potentially improving the delivery of treatment and diagnostic capabilities without the need for catheter exchange.

20 Claims, 3 Drawing Sheets

ALL-IN-ONE DELIVERY SHEATH/CATHETER—NOORCATH

RELATED APPLICATION

Under provisions of 35 U.S.C. § 119(e), the Applicant claims benefit of U.S. Provisional Application No. 63/611,499 filed on Dec. 18, 2023, and having inventors in common, which is incorporated herein by reference in its entirety.

It is intended that the referenced application may be applicable to the concepts and embodiments disclosed herein, even if such concepts and embodiments are disclosed in the referenced application with different limitations and configurations and described using different examples and terminology.

FIELD OF DISCLOSURE

The present disclosure generally relates to medical devices used in minimally invasive procedures. More specifically, it pertains to catheter-based systems for performing endovascular interventions in various parts of the body, including the heart, peripheral vasculature, and other organ systems.

BACKGROUND

In some situations, endovascular procedures may require the use of multiple specialized catheters to perform different functions during a single intervention. For example, an angiography catheter may be used to visualize blood vessels, while a separate catheter may be needed for balloon angioplasty or stent placement. Thus, the conventional strategy is to exchange catheters multiple times during a procedure to access different vascular regions or perform various tasks. This often causes problems because the conventional strategy does not allow for continuous real-time visualization while simultaneously carrying out interventions. For example, switching between an angiography catheter and a treatment catheter may lead to loss of optimal positioning and increased procedure time.

Current endovascular catheters may have limited maneuverability within complex vascular anatomies. The fixed shape of many conventional catheters may make it challenging to navigate tortuous vessels or access certain vascular regions. Additionally, existing catheters typically serve a single primary function, such as angiography or stent delivery, necessitating the use of multiple devices for comprehensive procedures.

The process of exchanging catheters during an endovascular intervention may increase the risk of complications. Each catheter insertion and removal may potentially damage vessel walls, dislodge plaque, or lead to bleeding or clot formation. Furthermore, multiple catheter exchanges may prolong the overall procedure time, resulting in extended patient sedation and increased radiation exposure for both the patient and medical staff.

Inventory management of numerous specialized catheters may present logistical challenges for healthcare facilities. Maintaining stocks of various catheter types to be prepared for different procedures may increase costs and storage requirements. The use of multiple catheters per procedure may also contribute to higher overall healthcare expenses associated with endovascular interventions.

Accordingly, there is a need for an improved endovascular catheter capable of performing multiple functions.

BRIEF OVERVIEW

This brief overview is provided to introduce a selection of concepts in a simplified form that are further described below in the Detailed Description. This brief overview is not intended to identify key features or essential features of the claimed subject matter. Nor is this brief overview intended to be used to limit the claimed subject matter's scope.

In some embodiments, a catheter system may comprise a dual lumen catheter. The dual lumen catheter may comprise an inner lumen and an outer lumen. The inner lumen may be configured to accommodate interventional devices. The outer lumen may surround the inner lumen. The outer lumen may comprise a plurality of contrast injection ports. The outer lumen may comprise a shape-changing mechanism. The catheter system may comprise a rotation mechanism. The rotation mechanism may be coupled to a proximal end of the dual lumen catheter. The rotation mechanism may be configured to rotate the dual lumen catheter. The catheter system may comprise a locking mechanism. The locking mechanism may be configured to maintain a shape of the dual lumen catheter.

In other embodiments, a dual lumen catheter device may comprise an elongate body. The elongate body may have a proximal end and a distal end. The device may comprise an inner lumen. The inner lumen may extend from the proximal end to the distal end. The inner lumen may be configured to accommodate interventional devices. The device may comprise an outer lumen. The outer lumen may surround the inner lumen. The outer lumen may extend from the proximal end to the distal end. The outer lumen may comprise a plurality of contrast injection ports. The contrast injection ports may be distributed along a length of the outer lumen. The outer lumen may comprise a plurality of channels. The channels may house shape-changing elements. The device may comprise a rotation mechanism. The rotation mechanism may be at the proximal end. The rotation mechanism may be configured to rotate the elongate body. The device may comprise a locking mechanism. The locking mechanism may be at the proximal end. The locking mechanism may be configured to maintain a shape of the elongate body.

In still other embodiments, a catheter system may comprise a catheter body. The catheter body may have a proximal end and a distal end. The system may comprise a first lumen. The first lumen may extend from the proximal end to the distal end. The first lumen may be configured to accommodate interventional devices. The system may comprise a second lumen. The second lumen may surround the first lumen. The second lumen may extend from the proximal end to the distal end. The second lumen may comprise a plurality of contrast injection ports. The contrast injection ports may be distributed along a length of the second lumen. The second lumen may comprise a plurality of shape-control elements. The system may comprise a rotation mechanism. The rotation mechanism may be coupled to the proximal end of the catheter body. The rotation mechanism may be configured to rotate the catheter body. The system may comprise a shape-locking mechanism. The shape-locking mechanism may be configured to maintain a selected shape of the catheter body.

Both the foregoing brief overview and the following detailed description provide examples and are explanatory only. Accordingly, the foregoing brief overview and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicant. In addition, the drawings may contain other marks owned by third parties and are being used for illustrative purposes only. All rights to various trademarks and copyrights represented herein, except those belonging to their respective owners, are vested in and the property of the Applicant. The Applicant retains and reserves all rights in its trademarks and copyrights included herein, and grants permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure. In the drawings.

DETAILED DESCRIPTION

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely to provide a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such a term to mean based on the contextual use of the term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subject matter disclosed under the header.

The present disclosure includes many aspects and features. Moreover, while many aspects and features relate to, and are described in, the context of a dual-lumen catheter device, embodiments of the present disclosure are not limited to use only in this context.

I. Platform Overview

This overview is provided to introduce a selection of concepts in a simplified form that are further described below. This overview is not intended to identify key features or essential features of the claimed subject matter. Nor is this overview intended to be used to limit the claimed subject matter's scope.

A dual-lumen catheter may combine multiple functions into a single device. A catheter is a thin, flexible tube that doctors insert into blood vessels to perform various procedures. Currently, doctors often need to use several different catheters during a single procedure, swapping them out as needed. The present application discloses a new "all-in-one" catheter that may replace multiple specialized catheters with a single, versatile device. The dual-lumen catheter may be multifunctional, allowing for use in various procedures including (but not limited to) angioplasty, stenting, clot removal, and/or control of bleeding and/or interrupting the blood supply to treat tumors/cancers, and/or the like without needing to switch catheters.

The catheter may include a dual-lumen design. The catheter may include two separate channels running through it. The inner channel may accommodate tools such as (but not limited to) guidewires, balloons, stents. Additionally or alternatively, the inner channel may be configured for deployment of coils or similar structures for interrupting blood flow to control bleeding, such as (but not limited to) gastro-intestinal bleeding (e.g., from ulcers or colonic bleeding), and/or to treat various tumors and/or cancers. The outer channel may be used for providing contrast dye and/or other liquid for imaging or treatment purposes. The design allows contrast dye to be injected while performing procedures, enabling continuous X-ray visualization.

The catheter may be bent into different shapes as needed during a procedure. Pull strings or other shape adjustment mechanisms that run along at least a portion of the length of the device may allow a user (e.g., a surgeon or other medical professional) to adjust a shape of the catheter during a procedure, without a need to remove the catheter from a patient (e.g., a human or animal undergoing surgery). Moreover, the entire catheter may be rotated in place, giving users more control and flexibility.

The improved dual-lumen catheter may increase patient safety, as fewer catheter exchanges means less risk to the patient. The catheter may also reduce procedure time, allow for a decrease in patient radiation exposure, and potentially save cost in terms of inventory and labor. The present dual-lumen catheter may replace many existing specialized catheters across a wide range of medical procedures involving blood vessels and/or other tubular structures in the body.

Embodiments of the present disclosure may comprise components including, but not limited to, at least:
A. A Catheter Body;
In some embodiments, the present disclosure may provide an additional set of components for further facilitating the catheter device. The additional set of components may comprise, but not be limited to:
B. A Shape Adjustment Mechanism;
C. A Rotational Control Mechanism.

Details with regards to each component are provided below. Although components are disclosed with specific functionality, it should be understood that functionality may be shared between components, with some functions split between multiple components, while other functions may be duplicated by the components. Furthermore, the name of each component should not be construed as limiting upon the functionality of the component. Moreover, each component and sub-component disclosed can be considered independently, without the context of the other components or sub-components. Each component may contain functionality defined in other portions of this specification. In the present disclosure, each component or subcomponent may be claimed on its own and/or interchangeably with other components or sub-components.

Both the foregoing overview and the following detailed description provide examples and are explanatory only. Accordingly, the foregoing overview and the following detailed description should not be considered to be restrictive. Further, features or variations may be provided in addition to those set forth herein. For example, embodiments may be directed to various feature combinations and sub-combinations described in the detailed description.

II. Platform Configuration

Embodiments of the present disclosure include catheters and uses thereof. By way of non-limiting example, FIGS. 1-5 illustrate a catheter system 100 may include a catheter body 102 having a proximal portion 104, a distal portion 106. The catheter body 102 may include a first (inner) lumen 108 extending therethrough and configured to allow transport of tools such as (but not limited to) guidewires, balloons, and/or stents in and out of a patient's body. The catheter body 102 may include a second (outer) lumen 110 that substantially surrounds the inner lumen 108 and is configured to allow for fluid to be delivered to particular locations within the patient body. In some embodiments, (e.g., where a procedure necessitates complex negotiations of several blood vessels), the catheter 100 may further incorporate negotiation mechanisms, such as a shape adjustment mechanism 120 and/or a rotational control mechanism 130.

Accordingly, embodiments of the present disclosure provide a set of components, including, but not limited to:
A. A Catheter Body The catheter system 100 may include a catheter body 102. The catheter body 102 may comprise an elongate flexible structure extending from a proximal portion 104 to a distal portion 106. In embodiments, the catheter body 102 may be generally straight. Alternatively, the catheter body 102 may be curved at the distal portion 106. In some embodiments, the catheter device 100 may include a catheter body 102 having a fixed shape. The fixed-shape device may be useful in, for example, simple interventions where no change in catheter shape is required. In other embodiments, the catheter 100 may include one or more mechanisms to control a shape and/or orientation of the catheter body 102. The shape changing embodiments may be useful in complex interventions that require navigation through multiple blood vessels or other anatomical features.

The catheter body 102 may include a first lumen 108 or internal passage extending longitudinally through the catheter body 102 from the proximal portion 104 to the distal portion 106. The first lumen 108 may be configured to accommodate interventional devices such as (but not limited to) guidewires, balloons, and/or stents.

The catheter body 102 may further include a second lumen 110 surrounding the first lumen 108 and extending longitudinally from the proximal portion 104 to the distal portion 106. In some embodiments, the second lumen 110 may be divided into multiple sections. For example, (e.g., where the catheter device 100 includes a shape adjustment mechanism 120) the second lumen 110 may include one or more closed tubular sections 112 and one or more open channel sections 114.

The second lumen 110 may optionally include one or more luminal dividers that serve to compartmentalize the channel into distinct sections. These dividers may be strategically integrated within the second lumen to enhance the functionality and control of fluid flow during medical procedures.

Each luminal divider may be constructed from a biocompatible material that ensures compatibility and safety when inserted into a patient's vascular system. Materials such as medical-grade polymers or metals that are commonly used in catheter construction, like silicone or stainless steel, may be utilized, depending on the specific requirements of the procedure and the desired flexibility or rigidity of the dividers.

The luminal dividers may aid in controlling and/or directing flow of fluids within the second lumen 110. By compartmentalizing the lumen 110, the dividers allow for selective, targeted delivery of fluids through specific delivery apertures 118 associated with each compartment. This targeted delivery may be useful for procedures requiring precise application of contrast agents or other fluids.

Each closed tubular section 112 of the second lumen 110 may include at least one injection port 116. For example, the closed tubular section 112 may include a plurality of injection ports 116 distributed along the length of the tubular section 112. The tubular section 112 may further comprise one or more delivery apertures 118 in fluid communication with the one or more injection ports 116. Each injection port 116 may be in fluid communication with the delivery apertures 118 via the closed tubular section 112 to allow delivery of a fluid material via the delivery apertures. The delivery apertures 118 may be configured in various sizes, shapes, and arrangements to optimize the delivery of fluids during medical procedures. As an example, the size of each aperture 118 may range between 0.1 mm to 2 mm in diameter, depending on the intended application and the viscosity of the fluids to be delivered. This size range helps to ensure an adequate flow rate while preventing unwanted leakage or blockage. The shapes of the apertures 118 may include circular, oval, and/or slit-like configurations. Each shape may be selected based on the desired flow characteristics and the specific medical procedure requirements. For instance, circular apertures may provide a more focused flow, whereas slits may offer a wider distribution of the fluid. In terms of arrangement, the apertures 118 may be evenly spaced along the length of the second lumen 110 to ensure uniform delivery of fluids. Alternatively, the apertures 118 may be disposed only near a distal end of the second lumen 110, allowing for focused delivery of fluid at or near the operative end of the catheter body 102.

As one non-limiting example, the injection port 116 may be used to deliver contrast material for fluoroscopic imaging during procedures. In embodiments, the injection ports 116 may be contrast delivery ports. The contrast delivery ports are in fluid communication with the delivery apertures 118 defined within the second lumen 110 of the catheter body 102. This arrangement may allow for an effective and evenly distributed delivery of contrast media to the surrounding vascular or anatomical structures. Each contrast delivery port 116 may be strategically positioned to optimize the coverage and effectiveness of the imaging process, thereby enhancing the visibility of the operational area during the procedure.

Figure 1:
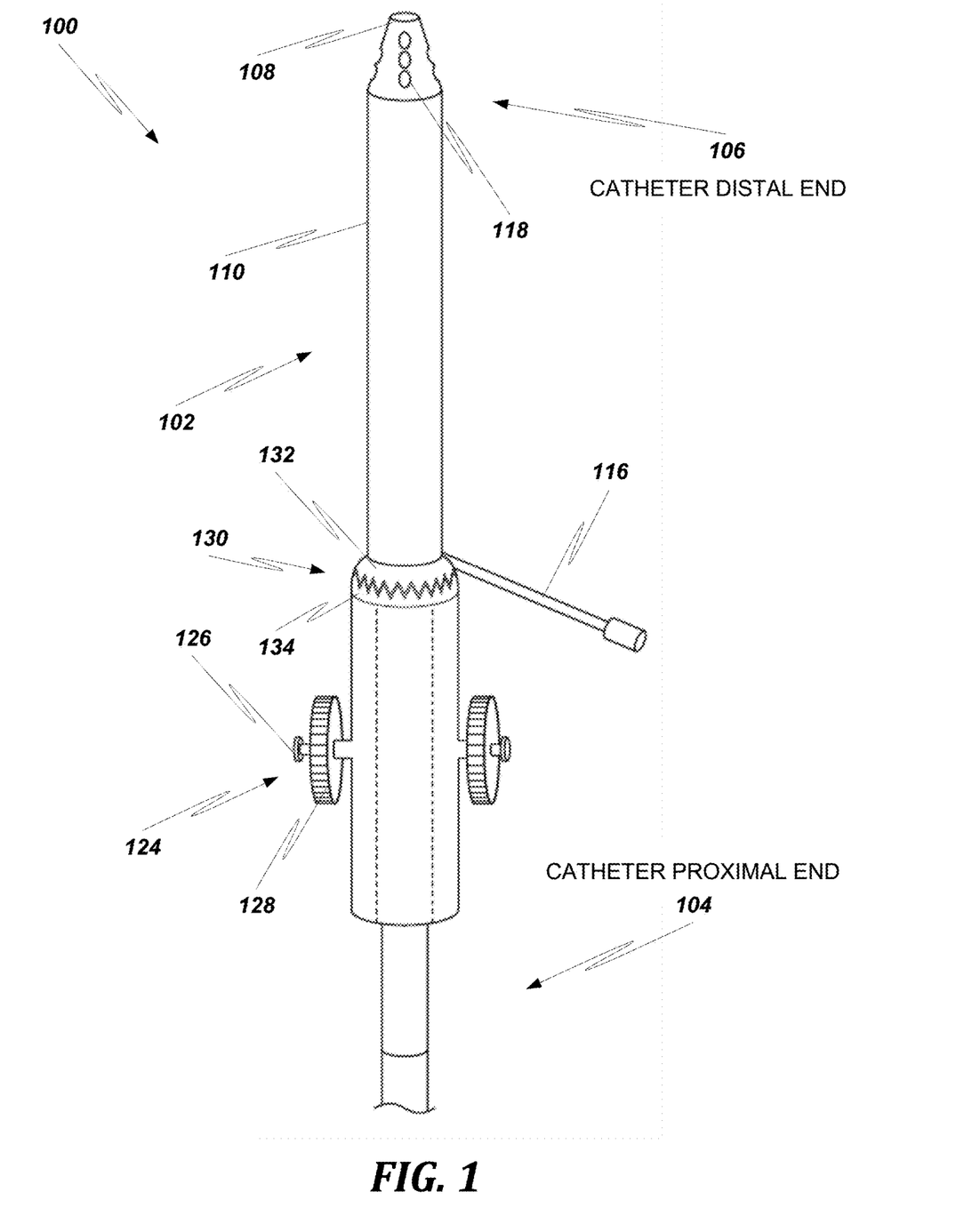
FIG. 1 illustrates an embodiment of a dual-lumen catheter system consistent with the present disclosure.
Figure 2:
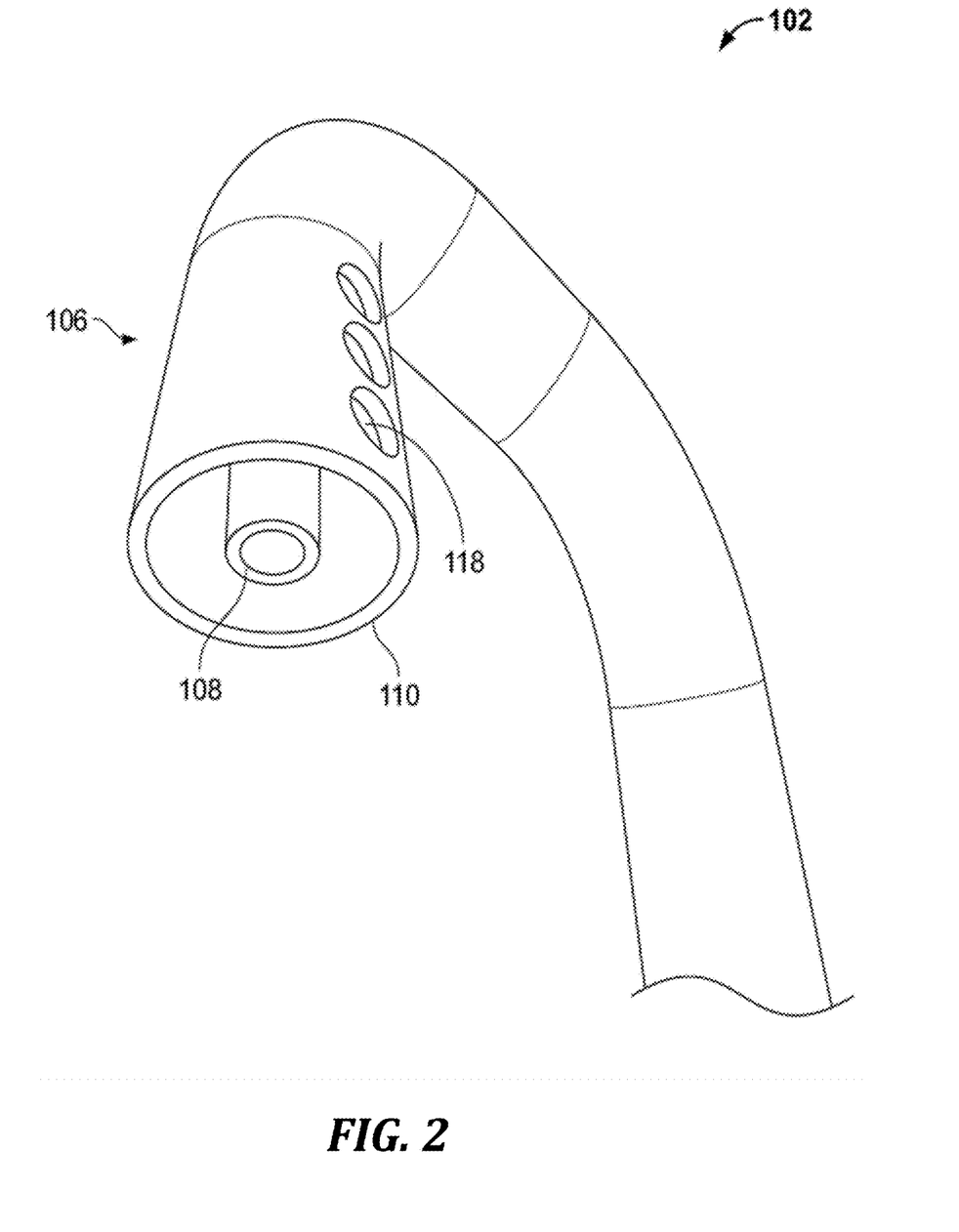
FIG. 2 is a detailed view of a distal portion of the dual-lumen catheter body of FIG. 2, shown in a bent configuration.
Figure 3:
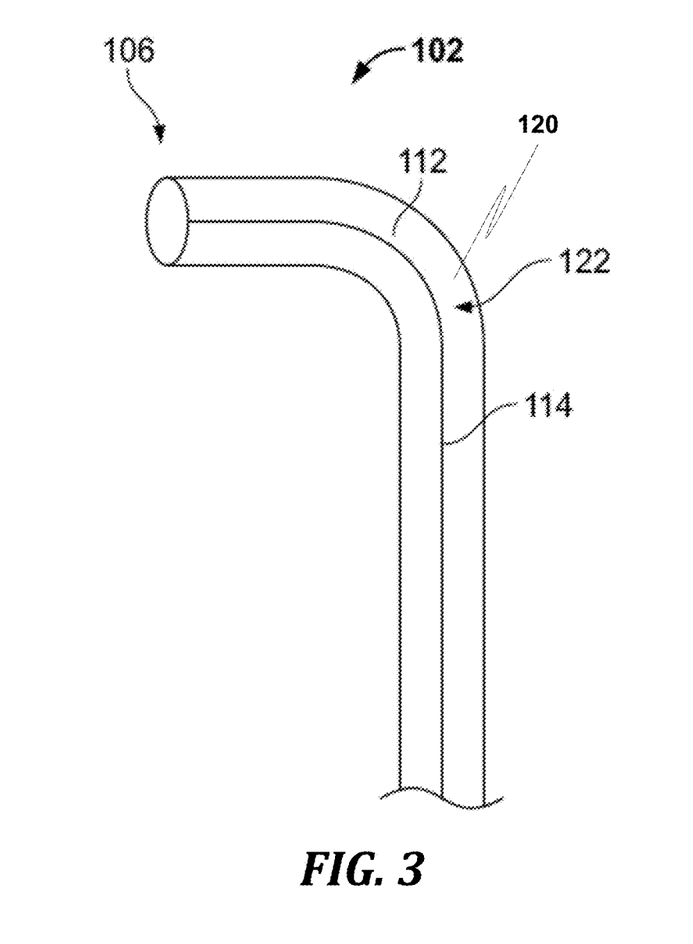
FIG. 3 is a side view of a distal portion of the dual-lumen catheter body of FIG. 2, shown in a bent configuration.

As shown in FIG. 1, the catheter body 102 may include a cap disposed at the distal end 106. The cap may cover the outer lumen (e.g., to help reduce or eliminate backflow), leaving the inner lumen open for intervention. In embodiments, the cap may include delivery apertures 118.

Moreover, the configuration of the injection ports 116 may be designed to prevent backflow or leakage, ensuring that the contrast media is delivered efficiently and effectively to the target area without wastage or unintended dispersion. This feature may help to reduce the volume of contrast media required, thereby minimizing potential toxicity or adverse reactions in patients.

In some embodiments, the injection ports 116 may be equipped with microvalves or other control mechanisms that regulate the flow of media (e.g., contrast media) injected via the ports. These microvalves may be operated manually or automatically. The inclusion of such control mechanisms may further refine the delivery process, allowing for precise adjustments in real-time during the procedure.

Each open channel section 114 of the second lumen 110 may house components of a shape adjustment mechanism 120. For example, the open channel sections 114 may accommodate pull wires, shape memory elements, or other structures that can alter the shape of the catheter body 102 when actuated including any mechanical, electronic, and/or other mechanism presently available or developed in the future.

In some embodiments, the second lumen 110 may include two or more closed tubular sections 112 and two or more open channel sections 114. The closed tubular sections 112 and open channel sections 114 may be arranged in an alternating pattern around the circumference of the catheter body 102. This arrangement may provide balanced fluid delivery and shape control.

The closed tubular sections 112 and open channel sections 114 may extend along different longitudinal portions of the catheter body 102. For example, the closed tubular sections 112 may extend along a distal portion of the catheter body 102 to allow contrast injection near the distal tip. The open channel sections 114 may extend along a more proximal portion to enable shape adjustment along the length of the catheter.

The second lumen 110 may transition between closed tubular sections 112 and open channel sections 114 at various points along the catheter body 102. These transition regions may be configured to maintain fluid isolation between the closed and open sections while allowing components like pull wires to pass between sections as needed.

The catheter body 102 may be formed of flexible, biocompatible materials suitable for intravascular use. For example, the catheter body 102 may be formed from plastic, nylon, and/or any other flexible, biocompatible material presently available or developed in the future. In some embodiments, the catheter body may have variable stiffness along its length to provide improved control and navigation capabilities for a user. As one example, the proximal portion 104 of the catheter body 102 may be stiffer than the distal portion 106 to enhance pushability and/or torque transmission. The distal portion 106 may be more flexible to allow for atraumatic navigation through tortuous vasculature.

In some embodiments, the catheter body 102 may include one or more radiopaque markers to enhance visibility under fluoroscopic imaging. The one or more radiopaque markers may be distributed along the length of the catheter body 102. For example, radiopaque marker bands may be positioned at a distal tip of the catheter body 102 and at predetermined intervals along the catheter body. The radiopaque markers may be formed of materials such as (but not limited to) platinum, gold, tantalum, and or other biocompatible, radiopaque materials.

In some embodiments, the outer surface of the catheter body 102 may include a lubricious coating to reduce friction during insertion and navigation through blood vessels. The coating may be any hydrophilic or hydrophobic polymer currently in existence or developed in the future. The inner surface of the first lumen 108 may include a lubricious coating to facilitate smooth passage of interventional devices therethrough.

The catheter body 102 may have a size in the range of about 2 French to 12 French (e.g., an outer diameter in the range of 0.67 mm to 4 mm), although larger and/or smaller catheter sizes are contemplated as being within the scope of this disclosure, depending at least on the intended application. The first lumen 108 may have an inner diameter sized to accommodate standard guidewires and/or any interventional devices. In particular, the first lumen 108 may have an inner diameter in the range of 0.010 inches to 0.027 inches. The wall thickness between the first lumen 108 and/or second lumen 110 may be selected to provide sufficient column strength while maintaining flexibility. The length of the catheter may vary (from very short to very long) based on the length of the path traveled in the body for the needed intervention.

In some embodiments, the catheter body 102 may include reinforcement structures, such as a braided or coiled wire embedded within the catheter wall. The reinforcement may provide enhanced torque transmission and/or kink resistance. The reinforcement may extend along the full length of the catheter body 102 or may be limited to specific sections thereof.

B. A Shape Adjustment Mechanism

The catheter system 100 may optionally include a shape adjustment mechanism 120. The shape adjustment mechanism may include any presently available or future developed mechanism, manual or mechanized, that may be used or applied to change the shape of at least the distal portion 106 of the catheter body 102. In some embodiments, the optional shape adjustment mechanism 120 may comprise: a plurality of longitudinal elements 122, a control mechanism 124, and a locking mechanism 126.

Each longitudinal element 122, of the plurality of longitudinal elements, may extend within the catheter body 102 from the distal portion 104 to the proximal portion 106. The longitudinal elements 122 may be pull wires, shape memory alloy elements, or other flexible structures capable of altering the shape of the catheter body 102 when actuated. For example, the longitudinal element 122 may be any mechanical and/or electrical component currently existing or developed in the future, that can alter the curvature of at least the distal end of the catheter.

The longitudinal elements 122 of the shape adjustment mechanism 120 may extend within the open channel sections 114 of the second lumen 110. Each longitudinal element 122 may be anchored at or near the distal portion 106 of the catheter body 102. The longitudinal elements 122 may extend proximally through the open channel sections 114 to the proximal portion 104 of the catheter body 102.

In some embodiments, the longitudinal elements 122 may comprise pull wires formed of a flexible yet strong material such as stainless steel, nitinol, or high-strength polymer fibers. The pull wires may have a diameter in the range of about 0.1 mm to 0.5 mm, although larger or smaller diameters are contemplated depending on the size of the catheter and desired flexibility.

In other embodiments, the longitudinal elements 122 may comprise shape memory alloy elements, such as nitinol wires or strips. The shape memory elements may be configured to assume a predetermined curved or bent shape when heated above a transition temperature, such as by application of electrical current.

The longitudinal elements 122 may be distributed circumferentially around the catheter body 102. As one specific example, in some embodiments, four longitudinal elements may be spaced at approximately 90 degree intervals around the circumference of the catheter body. This arrangement may allow for multi-directional shape adjustment of the catheter body 102. However, those of skill in the art will recognize that more or fewer longitudinal elements may be incorporated into the catheter body.

Each longitudinal element 122 may be independently actuatable to provide fine control over the catheter shape. For instance, applying tension to a single longitudinal element 122 on one side of the catheter may cause bending in that direction, while applying tension to multiple elements simultaneously may produce compound curves.

The proximal ends of the longitudinal elements 122 may be coupled to the control mechanism 124 at the proximal portion 104 of the catheter body 102. The control mechanism 124 may comprise actuators, such as sliders, knobs, or levers, that allow a user to selectively actuate one or more of the longitudinal elements 122. As a particular example, the longitudinal elements 122 may be formed as pull wires operatively connected to the user-operable control mechanism 124. This connection enables manipulation of the catheter's shape during medical procedures. The user-operable control mechanism may include a series of controls that the user can adjust to exert varying degrees of tension or slack on the pull wires.

The function of this connection is to provide precise control over the catheter shape without requiring manual adjustment at the catheter tip. This feature is useful during complex interventions, where the catheter must navigate through intricate vascular pathways. By adjusting the pull wires via the user-operable control mechanism, the physician may modify the shape of the catheter to conform to the pathway's contours, aiding in the effective placement of therapeutic devices or the performance of diagnostic procedures. The control mechanism 124 may be disposed at or near the proximal portion 104 of the catheter body 102. The control mechanism 124 may be operatively connected to the longitudinal elements 122. The control mechanism 124 may include one or more actuators 128. The one or more actuators may include, as non-limiting examples, one or more knobs, levers, and/or sliders, that allow a user to selectively actuate individual ones of the plurality of longitudinal elements 122.

The control mechanism 124 may comprise one or more actuators 128 operatively connected to the longitudinal elements 122. The one or more actuators 128 may be configured to selectively actuate individual longitudinal elements 122 or groups of longitudinal elements 122. In some embodiments, the one or more actuators 128 may comprise sliders that can be moved longitudinally to increase or decrease tension on associated longitudinal elements 122. The sliders may be arranged circumferentially around the proximal portion 104 of the catheter body 102 to correspond with the positions of the longitudinal elements 122.

In other embodiments, the one or more actuators 128 may comprise rotatable knobs or dials. Rotation of a knob or dial in one direction may increase tension on an associated longitudinal element 122, while rotation in the opposite direction may decrease tension. The knobs or dials may be arranged radially around the proximal portion 104 of the catheter body 102.

In yet other embodiments (e.g., where a longitudinal element 122 is formed from a shape memory material), actuation of the longitudinal element 122 may include altering a temperature of the element. For example, an actuator 128 may cause electrical current to flow through a longitudinal element 122, increasing the temperature of the element. When the element temperature exceeds a transition threshold value, the shape memory material may transition to a different shape, thereby adjusting the curve of the catheter body 102.

The control mechanism 124 may further comprise a user interface to facilitate precise control of the longitudinal elements 122. For example, the user interface may include visual indicators showing the current tension or position of each longitudinal element 122. In some embodiments, the user interface may comprise a touchscreen display allowing the operator to adjust tensions via a graphical interface.

The control mechanism 124 may be configured to allow individual and/or coordinated actuation of the longitudinal elements 122. For instance, the control mechanism 124 may include preset configurations that simultaneously adjust multiple longitudinal elements 122 to achieve common catheter shapes, such as J-curves or S-curves. These preset configurations may be activated via dedicated buttons or through a software interface.

In some embodiments, the control mechanism 124 may incorporate force feedback to provide the operator with tactile information about the forces being applied to the catheter tip. This feedback may help prevent excessive force application that could potentially damage vessel walls. The control mechanism 124 may also include safety features to prevent over-tensioning of the longitudinal elements 122. For example, the control mechanism 124 may incorporate mechanical stops or electronic limits to restrict the maximum tension that can be applied to each longitudinal element 122.

The locking mechanism 126 may be integrated with the control mechanism 124 to maintain the catheter body 102 in a desired shape once it has been achieved. The locking mechanism 126 may comprise mechanical clamps, friction locks, or other suitable mechanisms to secure the positions of the longitudinal elements 122 relative to the catheter body 102.

In some embodiments, the locking mechanism 126 may allow for partial locking, wherein some longitudinal elements 122 are fixed while others remain adjustable. This feature may enable fine-tuning of the catheter shape while maintaining a general configuration.

The control mechanism 124 and locking mechanism 126 may be designed for one-handed operation, allowing the operator to manipulate the catheter shape while simultaneously performing other tasks. The mechanisms may be ergonomically shaped and positioned for ease of use during extended procedures.

In certain embodiments, the control mechanism 124 may be removable from the catheter body 102. This feature may allow for easier cleaning and sterilization of the catheter system 100 between uses. The removable control mechanism 124 may connect to the catheter body 102 via a standardized interface, potentially allowing for a single control mechanism 124 to be used interchangeability between different individual catheter bodies 102, and/or with different catheter models or sizes.

The control mechanism 124 may be battery-powered or connected to an external power source. In some embodiments, the control mechanism 124 may include a rechargeable battery to provide portability and ease of use in various clinical settings.

Overall, the control mechanism 124 and locking mechanism 126 may work in concert to provide precise, intuitive control over the shape and position of the catheter body 102, enhancing the operator's ability to navigate complex vasculature and perform intricate procedures with greater efficiency and safety.

The shape adjustment mechanism 120 may be designed to work in conjunction with the rotational control mechanism 130, allowing the catheter to maintain its shape while being rotated. This combination of shape adjustment and rotation may provide enhanced maneuverability and positioning capabilities.

C. A Rotational Control Mechanism

The catheter system 100 may optionally include a rotational control mechanism 130. The rotational control mechanism 130 may be coupled to the proximal portion 104 of the catheter body 102. The rotational control mechanism 130 may be configured to rotate at least a portion of the catheter body 102 about its longitudinal axis.

Figure 4:
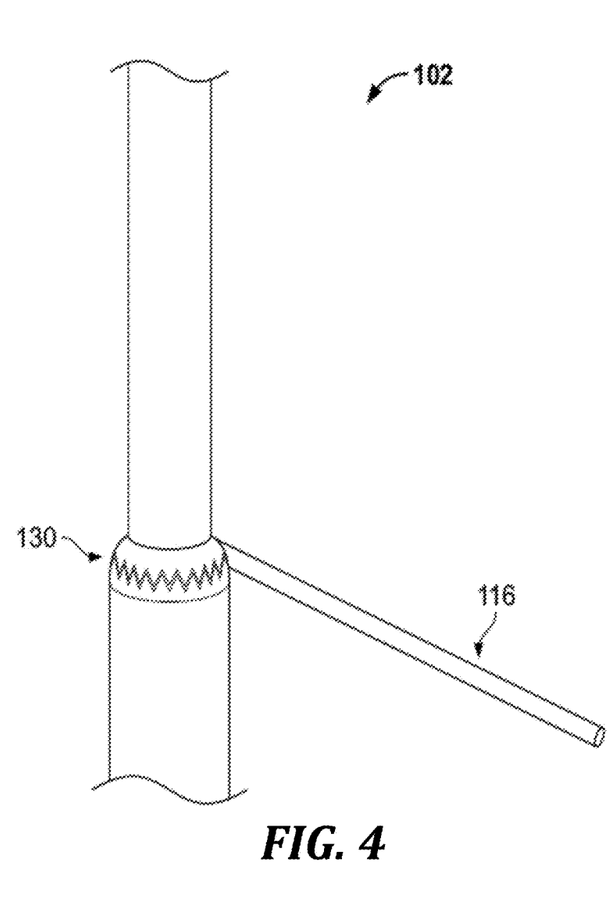
FIG. 4 is a detailed view of a rotation mechanism for use with the dual-lumen catheter system of FIG. 1.

The rotational control mechanism 130 may comprise a rotatable member 132 and a fixed member 134. The rotatable member 132 may be coupled to the catheter body 102. The fixed member 134 may be configured to remain stationary.

In some embodiments, the rotatable member 132 may comprise a wheel or dial. The wheel or dial may be sized and shaped for manipulation by a user's fingers. The wheel or dial may include surface features, such as ridges or texturing, to enhance grip.

The fixed member 134 may comprise a housing or base that supports the rotatable member 132. The fixed member 134 may be configured for attachment to a procedure table or other stationary surface.

In some embodiments, the rotational control mechanism 130 may include a gear system coupling the rotatable member 132 to the catheter body 102. The gear system may provide a mechanical advantage, allowing precise rotational control of the catheter body 102.

The rotational control mechanism 130 may include markings or indicators to show the degree of rotation. For example, the fixed member 134 may include degree markings, while the rotatable member 132 may include an indicator line.

In some embodiments, the rotational control mechanism 130 may include a locking feature. The locking feature may be configured to selectively prevent rotation of the catheter body 102. This may allow the operator to maintain a desired rotational orientation during a procedure.

The rotational control mechanism 130 may be designed to operate in conjunction with the shape adjustment mechanism 120. This may allow the operator to rotate the catheter body 102 while maintaining a desired shape.

In some embodiments, the rotational control mechanism 130 may include sensors to detect the rotational position of the catheter body 102. The sensors may provide feedback to the operator or to an automated control system.

The rotational control mechanism 130 may be removable from the catheter body 102. This may allow for easier cleaning and sterilization of the catheter system 100 between uses.

III. Platform Operation

Embodiments of the present disclosure provide device operative by a set of methods. The following depicts an example of at least one method of a plurality of methods that may be performed using the device.

Although the stages of the following example method are disclosed in a particular order, it should be understood that the order is disclosed for illustrative purposes only. Stages may be combined, separated, reordered, and various intermediary stages may exist. Accordingly, it should be understood that the various stages, in various embodiments, may be performed in arrangements that differ from the ones described below. Moreover, various stages may be added or removed from the method without altering or departing from the fundamental scope of the depicted methods and systems disclosed herein.

The catheter system 100 may be used in a variety of medical procedures involving blood vessels and other tubular structures in the body. In some embodiments, the catheter system 100 may be utilized in cardiovascular procedures such as coronary angiography, angioplasty, and stenting. The catheter system 100 may also be employed in peripheral vascular procedures, neurovascular procedures, endovenous procedures, gastrointestinal procedures, and interventional oncology procedures.

In embodiments, the catheter system 100 may be useful across a variety of medical procedures, including, but not limited to: cardio-vascular procedures (e.g., coronary angiography with or without angioplasty/stenting,) peripheral vascular procedures (e.g., upper and/or lower extremity endovascular procedures; abdominal visceral endovascular procedures; carotid endovascular procedures; thoracic endovascular procedures, etc.), neuro-vascular procedures, endovenous procedures, gastrointestinal endoscopic procedures, hepato-biliary endoscopic procedures, pancreatic endoscopic procedures, pulmonary bronchoscopic procedures, interventional oncology procedures, and/or any other procedure (existing presently or developed in the future) that requires use of a catheter, and particularly those that require the use of multiple conventional catheters.

To use the catheter system 100, a medical practitioner may first prepare the patient and establish vascular access using standard techniques. The catheter body 102 may then be inserted into the patient's vasculature through an appropriate access site, such as the femoral artery, radial artery, or brachial artery. The catheter may also be inserted through any venous system for any endo-venous interventions such as (but not limited to) clot dissolution or retrieval, valvulotomy, and/or the like. The catheter may also be inserted through endoscopes for procedures that involve the gastrointestinal; colonic; hepato-biliary; pancreatic duct diagnostics and/or interventions. The catheter may also be introduced through bronchoscopes for any endo-bronchial procedures.

The practitioner may advance the catheter body 102 through the patient's blood vessels, gastrointestinal tract, pulmonary system, and/or the like under fluoroscopic guidance.

During advancement of the catheter body 102, the practitioner may inject contrast material through the injection ports 116 of the second lumen 110. The contrast material may exit through the delivery apertures 118, allowing visualization of the blood vessels under fluoroscopy. This real-time imaging may enable the practitioner to navigate the catheter body 102 to the desired location within the patient's vasculature.

As the catheter body 102 is advanced, the practitioner may utilize the shape adjustment mechanism 120 to alter the shape of the catheter body 102 as needed to navigate through tortuous or complex vascular anatomy. The practitioner may manipulate the one or more actuators 128 of the control mechanism 124 to selectively tension or relax the longitudinal elements 122, thereby adjusting the curvature of the catheter body 102. Once a desired shape is achieved, the locking mechanism 126 may be engaged to maintain the catheter body 102 in that configuration.

The rotational control mechanism 130 may be employed to rotate the catheter body 102 about its longitudinal axis. This rotation may allow the practitioner to orient the distal portion 106 of the catheter body 102 in a desired direction, such as to align with a branch vessel or to position the delivery apertures 118 for optimal contrast delivery.

Once the catheter body 102 is positioned at the target location, the practitioner may perform various interventional procedures using devices inserted through the first lumen 108. For example, a guidewire may be advanced through the first lumen 108 to cross a lesion or blockage in a blood vessel. Subsequently, a balloon catheter may be introduced over the guidewire through the first lumen 108 to perform angioplasty. If stenting is required, a stent delivery system may be advanced through the first lumen 108 to deploy a stent at the treatment site.

Throughout the procedure, the practitioner may continue to inject contrast material through the second lumen 110 to visualize the treatment area and assess the results of the intervention. The ability to perform these multiple functions without exchanging catheters may reduce procedure time, decrease the risk of complications associated with catheter exchanges, and minimize radiation exposure to both the patient and medical staff.

In some embodiments, the catheter system 100 may be used for clot removal procedures. The practitioner may navigate the catheter body 102 to the site of a blood clot using the shape adjustment mechanism 120 and rotational control mechanism 130. A clot retrieval device may then be advanced through the first lumen 108 to capture and remove the clot. The ability to adjust the catheter shape and inject contrast material during the procedure may enhance the practitioner's ability to safely and effectively remove the clot. Alternatively or additionally, the catheter, using the contrast injection may be used to precisely place embolic coils to interrupt blood supply to a tumor for therapeutic intervention.

For interventional oncology procedures, the catheter system 100 may be used to deliver embolic agents or chemotherapeutic drugs to tumors. The practitioner may position the catheter body 102 in the blood vessels supplying the tumor, using contrast injection through the second lumen 110 to confirm proper placement. The therapeutic agents may then be delivered through the first lumen 108 while maintaining the ability to monitor the procedure with ongoing contrast injections.

In gastrointestinal or hepatobiliary procedures, the catheter system 100 may be advanced through the appropriate anatomical structures to reach the target area. The shape adjustment mechanism 120 may be particularly useful in navigating the complex anatomy of these systems. Once in position, various interventional devices may be introduced through the first lumen 108 to perform diagnostic or therapeutic procedures.

The versatility of the catheter system 100 may allow for its use in a wide range of medical procedures, potentially reducing the need for multiple specialized catheters and simplifying inventory management for healthcare facilities. The ability to perform multiple functions with a single device may lead to more efficient and cost-effective patient care.

VI. Claims

While the specification includes examples, the disclosure's scope is indicated by the following claims. Furthermore, while the specification has been described in language specific to structural features and/or methodological acts, the claims are not limited to the features or acts described above. Rather, the specific features and acts described above are disclosed as examples for embodiments of the disclosure.

Insofar as the description above and the accompanying drawing disclose any additional subject matter that is not within the scope of the claims below, the disclosures are not dedicated to the public and the right to file one or more applications to claims such additional disclosures is reserved.

The following is claimed:

1. A delivery catheter apparatus for performing an angiographic intervention comprising:
   a catheter body having a proximal end and a distal end, the catheter body comprising:
      a first lumen extending longitudinally through the catheter body from the proximal end to the distal end, the first lumen configured to receive an interventional device and an associated procedure catheter;
      a second lumen surrounding the first lumen and extending longitudinally from the proximal end to the distal end, the second lumen defining a plurality of delivery apertures; and
      a plurality of injection ports along its length, each of the plurality of injection ports being in fluid communication with at least one of the plurality of delivery apertures.

2. The delivery catheter apparatus of claim 1, wherein the second lumen further comprises a plurality of shape-control elements configured to adjust the shape of the catheter body.

3. The delivery catheter apparatus of claim 1, further comprising a rotational control mechanism coupled to the proximal end of the catheter body and configured to rotate the catheter body while maintaining its shape.

4. The delivery catheter apparatus of claim 1, wherein the plurality of delivery apertures are configured to facilitate real-time fluoroscopic imaging during an interventional procedure.

5. The delivery catheter apparatus of claim 1, wherein the catheter body is configured to perform an interventional procedure without the need for catheter exchange.

6. The delivery catheter apparatus of claim 1, wherein the catheter body comprises a radiopaque marker at the distal end to facilitate positioning of the catheter apparatus under imaging guidance.

7. The delivery catheter apparatus of claim 1, wherein the catheter body comprises a biocompatible polymer material having sufficient flexibility to navigate through tortuous vasculature while maintaining structural integrity.

8. The delivery catheter apparatus of claim 1, further comprising a fluid delivery system coupled to the proximal end of the catheter body and in fluid communication with the second lumen, the fluid delivery system configured to deliver contrast media through the plurality of delivery apertures.

9. The delivery catheter apparatus of claim 1, wherein the catheter body further comprises a hydrophilic coating on at least an outer surface of the catheter body to reduce friction during navigation through vasculature.

10. A delivery catheter system for performing an angiographic intervention comprising:
    a tubular member having a proximal terminal and a distal terminal, the tubular member comprising:
       a primary channel running from the proximal terminal to the distal terminal configured for insertion of a medical device using an associated procedure catheter;
       a secondary channel encasing the primary channel and extending from the proximal terminal to the distal terminal, the secondary channel comprising:
          one or more ports for the injection of imaging agents distributed along the tubular member; and
          a configuration altering mechanism embedded within the tubular member; and
          a configuration locking device at the proximal terminal designed to hold the tubular member in a specified configuration.

11. The delivery catheter system of claim 10, wherein the secondary channel further comprises a plurality of luminal dividers to compartmentalize the secondary channel.

12. The delivery catheter system of claim 10, wherein the primary channel is configured to accommodate a variety of medical devices including one or more of the following: guidewires, balloons, or stents.

13. The delivery catheter system of claim 10, wherein the tubular member is composed of a biocompatible material suitable for insertion into a patient's vascular system.

14. The delivery catheter system of claim 10, wherein the configuration altering mechanism further includes a rotational control mechanism coupled to the proximal terminal configured to facilitate 360-degree rotation of the tubular member while maintaining the specified configuration.

15. The delivery catheter system of claim 10, wherein the tubular member comprises at least one radiopaque marker to facilitate positioning under imaging guidance.

16. The delivery catheter system of claim 10, wherein the tubular member comprises a tapered distal portion to facilitate atraumatic navigation through tortuous vasculature.

17. The delivery catheter system of claim 10, wherein the tubular member comprises a biocompatible polymer material having sufficient flexibility to navigate through tortuous vasculature while maintaining structural integrity.

18. A delivery catheter system for performing an angiographic intervention comprising:
    a catheter body having a proximal end and a distal end, the catheter body comprising:
       a first lumen extending from the proximal end to the distal end, the first lumen configured to accommodate an interventional device via an associated procedure catheter;
       a second lumen surrounding the first lumen and extending from the proximal end to the distal end, the second lumen comprising:
          a plurality of contrast injection ports distributed along a length of the second lumen, and
          a plurality of shape-control elements;
       a rotation mechanism coupled to the proximal end of the catheter body and configured to rotate the catheter body; and
       a shape-locking mechanism configured to maintain a selected shape of the catheter body.

19. The delivery catheter system of claim 18, wherein catheter body comprises a tapered distal portion to facilitate atraumatic navigation through tortuous vasculature.

20. The delivery catheter system of claim 18, wherein the catheter body comprises a biocompatible polymer material having sufficient flexibility to navigate through tortuous vasculature while maintaining structural integrity.

* * * * *